United States Patent [19]

Gramnäs

[11] Patent Number: 5,800,566

[45] Date of Patent: Sep. 1, 1998

[54] ARTIFICIAL JOINT WITH A HYDRAULIC DAMPING CYLINDER

[76] Inventor: Finn Gramnäs, Brantalid 18, S-511 56 Kinna, Sweden

[21] Appl. No.: 351,296

[22] PCT Filed: Jun. 9, 1993

[86] PCT No.: PCT/SE93/00513

§ 371 Date: Jan. 23, 1995

§ 102(e) Date: Jan. 23, 1995

[87] PCT Pub. No.: WO93/25165

PCT Pub. Date: Dec. 23, 1993

[30] Foreign Application Priority Data

Jun. 9, 1992 [SE] Sweden .................................. 9201749
Aug. 28, 1992 [SE] Sweden .................................. 9202472

[51] Int. Cl.⁶ .............................................. A61F 2/64
[52] U.S. Cl. ................................. 623/39; 623/44; 623/45
[58] Field of Search .......................... 623/43, 44, 45, 623/50, 56, 39, 59–60; 188/312, 313, 302, 311, 318, 287, 286

[56] References Cited

U.S. PATENT DOCUMENTS

| | | | |
|---|---|---|---|
| 1,534,059 | 4/1925 | Dennett | 188/287 |
| 1,574,601 | 2/1926 | Brundage | 188/287 |
| 1,575,973 | 3/1926 | Coleman | 188/287 |
| 1,733,395 | 10/1929 | Blanchard | 188/287 |
| 2,667,644 | 2/1954 | Johnson | 623/44 |
| 3,054,136 | 9/1962 | Schlage et al. | 188/287 |
| 3,059,268 | 10/1962 | McHale | 188/287 |
| 3,201,110 | 8/1965 | Taccone | 188/287 |
| 3,307,842 | 3/1967 | Ellis, Jr. | 188/287 |
| 3,385,131 | 5/1968 | Hall et al. | 188/313 |
| 3,584,331 | 6/1971 | D'Hooge | 188/287 |
| 4,370,761 | 2/1983 | Serri | 623/43 |
| 4,937,913 | 7/1990 | Jentsch | 188/286 |
| 5,050,712 | 9/1991 | Heideman | 188/287 |
| 5,070,970 | 12/1991 | Johnston et al. | 188/318 |
| 5,171,325 | 12/1992 | Aulie | 623/43 |
| 5,376,138 | 12/1994 | Bouchard et al. | 623/44 |
| 5,405,407 | 4/1995 | Kodama et al. | 623/44 |

FOREIGN PATENT DOCUMENTS

| | | | |
|---|---|---|---|
| 0503775 | 4/1992 | European Pat. Off. | 623/44 |
| 1292763 | 2/1987 | U.S.S.R. | 623/45 |

*Primary Examiner*—John G. Weiss
*Assistant Examiner*—Bruce E. Snow
*Attorney, Agent, or Firm*—Birch, Stewart, Kolasch & Birch, LLP

[57] ABSTRACT

A device for damping of the turning movement of a joint such as an artificial knee joint is built into a bearing bridge of a joint. The joint can be a seven pivot point joint with a shaft of one of the pivot points being provided with a gear-wheel. The damping device includes a hydraulic cylinder with a piston connected to the gear-wheel. Channels with chokes and back valves connect the two sides of the piston of the hydraulic cylinder whereby adjustable damping in several steps can be achieved. A compact design for a joint and damping cylinder is achieved.

15 Claims, 3 Drawing Sheets

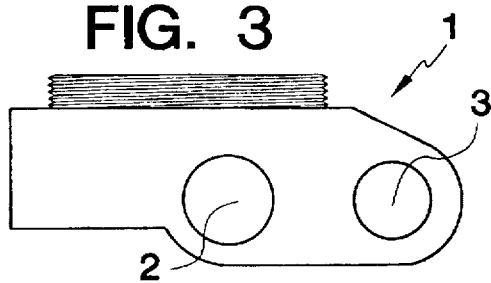
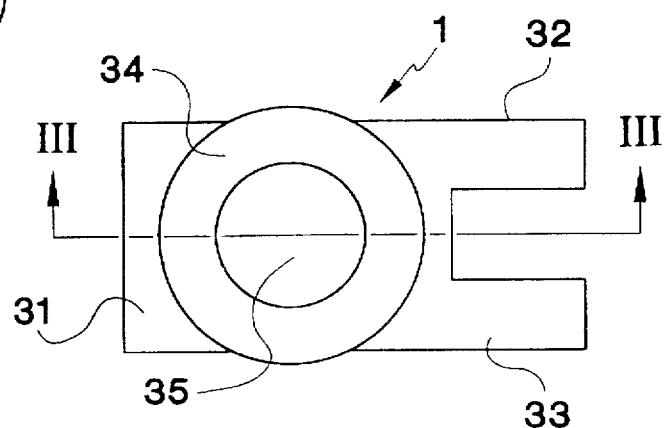
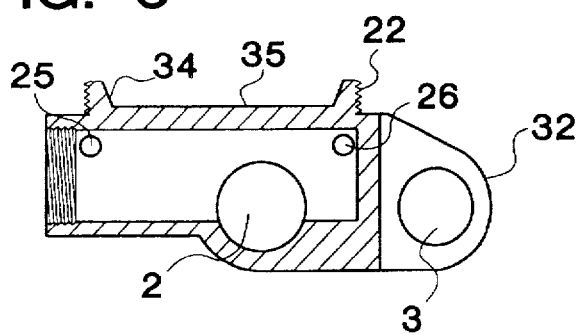
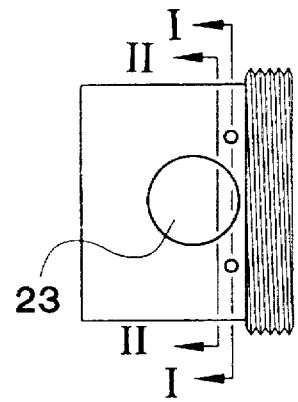
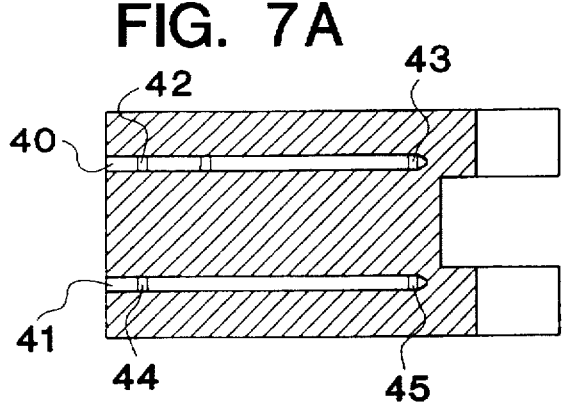
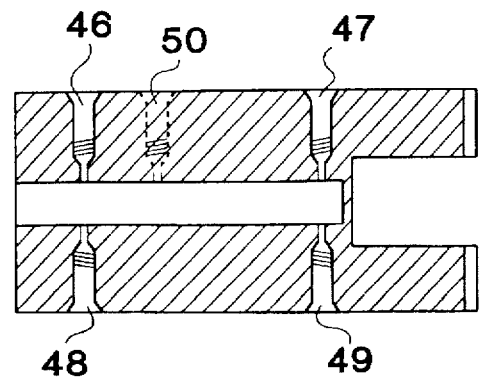

5,800,566

1

ARTIFICIAL JOINT WITH A HYDRAULIC DAMPING CYLINDER

FIELD OF THE INVENTION

The present invention relates to an artificial joint equipped with a hydraulic damping cylinder and a hydraulic damping cylinder designed to be a part of an artificial joint, especially of such an artificial knee joint, in which it is not possible to install conventional damping cylinders with a cylinder block into and out of which a piston rod reciprocates. The present invention is especially adapted to be used with artificial knee joints of the type with seven pivot points which is further described in the Swedish patent application no. 91001183-4 and PCT/SE91/00240, but damping cylinders according to the present invention can also be utilized with artificial joints of other types such as with polycentric knee joints with four pivot points and even with joints having one single pivot point.

The artificial joint type with seven pivot points which is described in the above mentioned patent publication makes great progress in relation to the previous state of the art. Equipped with a hydraulic damping cylinder as described below and according to the claims the joint is also given a control of the swing phase which, together with the quality of stability of the joint, produces an artificial knee joint which function very close to a natural leg despite the lack of active components to replace muscle force.

DESCRIPTION OF THE BACKGROUND ART

It is known in the art to arrange hydraulic damping cylinders with other artificial joints, see for instance EP 0097226. In its simplest design, the damping cylinder comprises a piston and channels with chokes in the cylinder between the opposite sides of the piston. The present invention also relies on this principle. But in the present invention, a piston rod moving into or out of the damping cylinder is not used, because it will involve disadvantages and difficulties in building such conventional damping cylinders into, for instance, knee joints with multiple pivot points as mentioned above.

It has also been known for a long time, from the Swiss patent publication no. 248 586, to arrange hydraulic damping cylinders in such a way that the longitudinal movement of the piston is directly transferred to a turning movement by means of gear teeth on the piston in mesh with a gearwheel. This construction, mainly intended for door closers, has a built in spring with a spring force acting on the piston in one direction while the piston includes a spring loaded valve opening on movement against the spring force and a channel damping the return movement. While this construction has been known since 1947, until the present invention no similar construction has been used with am artificial joint, or been adapted for it according to the present invention.

SUMMARY OF THE INVENTION

An object of the present invention is to achieve an artificial joint with multiple pivot points integrated with a hydraulic damping cylinder in such a way that it insignificantly adds length to the joint or otherwise deteriorates the function of the joint.

A second object is to achieve a damping cylinder, the damped movement of which consists of a turning of an axis instead of an axial movement, whereby tightening against leakage of hydraulic oil can better can be achieved.

A third object of the present invention is to bring about a damping cylinder in which the damping can take place in several stages with different magnitude.

2

A further object of the invention is to place the damping cylinder in such a way in the joint that heat produced in it will be dissipated to avoid too high a temperature.

These and other objects are achieved with an artificial joint and a damping cylinder having a piston having a rack-gearing along one side thereof. A hydraulic cylinder has a longitudinal opening in which the piston is mounted. The piston is completely contained within the cylinder and the piston being reciprocable in the hydraulic cylinder. The cylinder further has channels interconnecting opposed ends of the cylinder on opposite sides of the piston whereby hydraulic fluid can flow therethrough upon movement of the piston. Means are provided on an end of the cylinder for mounting a first link of the artificial joint to the hydraulic cylinder. Means for resisting movement of the hydraulic fluid through the channels are also provided. The means for resisting includes back valves for causing hydraulic fluid to flow in different channels for each direction of movement of the piston. A shaft has a gear mounted thereon and extends into the cylinder. The gear meshes with the rack-gearing of the piston. Only the shaft extends from an interior of the hydraulic cylinder while the piston and means for resisting are contained within the cylinder. A second link of the artificial joint is mounted to the shaft and movement of the shaft moves the hydraulic cylinder to thereby force hydraulic fluid through the channels of the piston. The means for resisting movement resists flow of hydraulic fluid to dampen movement of the shaft.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described more in detail with reference to the following drawings which are given by way of illustration only, and thus are not limitative of the present invention, and in which:

FIGS. 3–7A, 7B show different views, sections and details thereof;

DETAILED DESCRIPTION OF THE PREFERRED EMBODIMENTS

Figure 1:
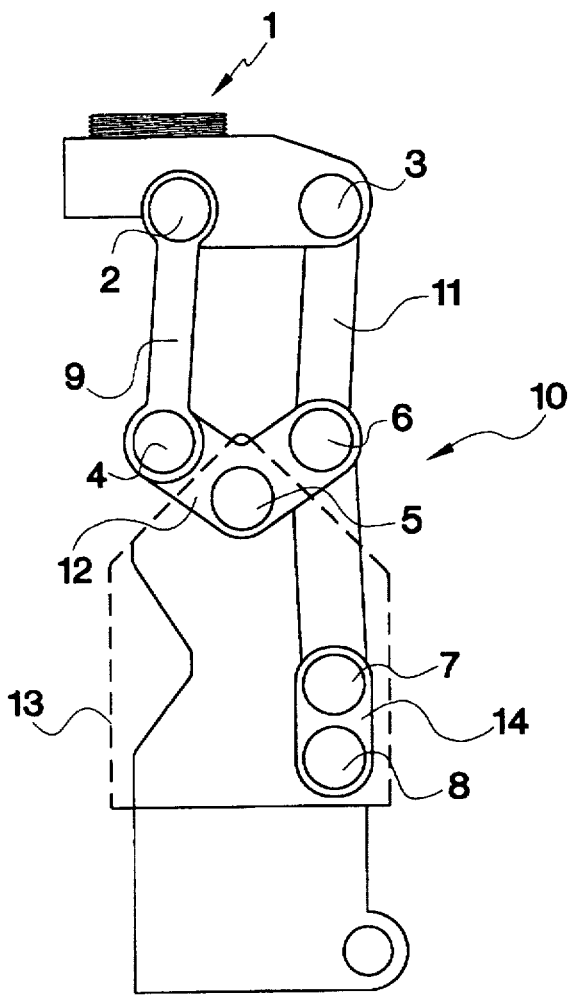
FIG. 1 shows a joint with seven pivot points comprising a pumphouse/upper bearing bridge (1) containing a damping cylinder according to the invention.

FIG. 1 shows an embodiment of a joint 10, which is described more in detail in the above mentioned Swedish and PCT patent application. It presents seven pivot point axes 2–8, one upper bearing bridge 1, a front link 9 with two pivot point axes, a back link 11 with three pivot point axes, a cradle or balance 12 with three pivot point axes and a lower locking link 14. The cradle or balance 12 joins the links 9 and 11 with a shank holder 13 at its upper pivot point axis 5. The lower locking link 14 has two pivot point axes connecting the back link 11 with the shank holder 13 at its lower pivot point axis 8. As described in more detail in the above mentioned patent applications, this construction with seven pivot points constitutes an especially advantageous artificial knee joint.

Figure 2:
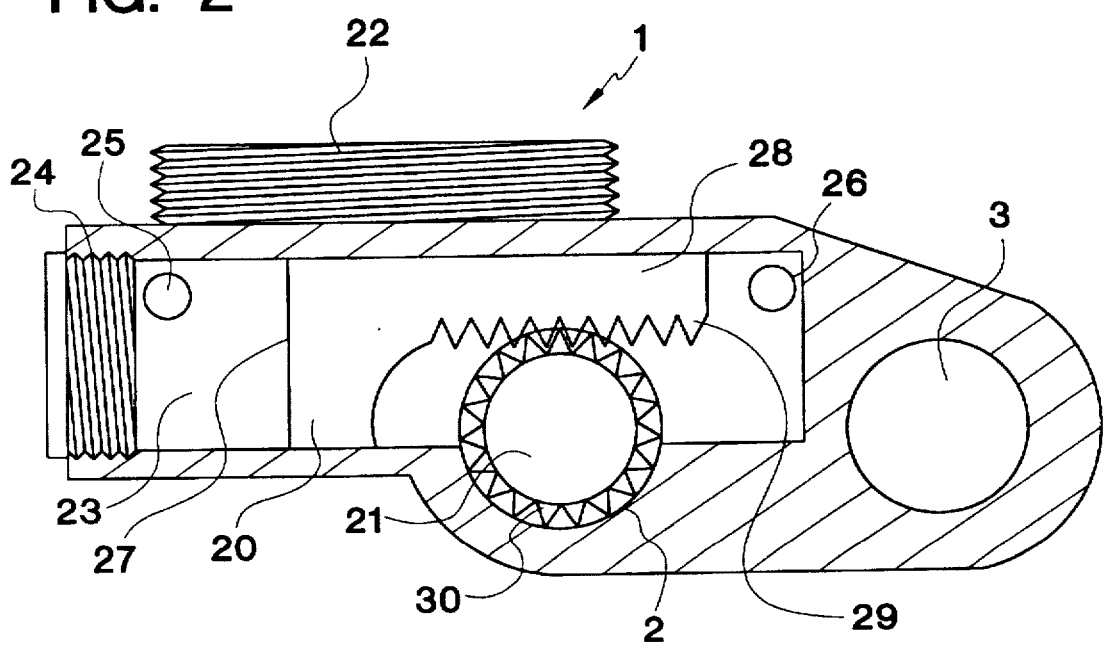
FIG. 2 shows partly in section the pump house in FIG. 1.

Known cylinder-piston-arrangements for regulation and damping of the swing movement of the lower-leg part can hardly be built into this joint because the construction will be heavy and clumsy or it will be too long. The hydraulic unit forming the damping cylinder according to the invention therefore has been built into the upper bearing bridge 1 which will thereby also work as a pump house as is shown in FIG. 2. Thus, the upper bearing bridge or pump house 1 is modelled in such a way that it has been provided with a cylindrical drill hole 23 perpendicular to and partly intersecting the hole for pivot point axis 2. The open side of the drill hole 23 is closed by a lid 24. The drill hole 23, which constitutes a hydraulic cylinder, contains a piston device 20 comprising a piston 27 with a fluid-tight fit in the drill hole 23. The piston device 20 also includes a second, elongated part 28 extending from the piston 27 and an axially arranged rack-gearing part 29. In the hole for the pivot point axis 2, a shaft 21 is arranged with a central gear-wheel part 30 meshing with rack-gearing part 29. Turning movement of shaft 21 is damped whereby the movement of the piston 27 is influenced by a choke of the flow in a channel for hydraulic fluid connected with the drill hole 23 on both sides of the piston 27 through the orifices 25 and 26. Sealings are arranged to prevent the hydraulic fluid from escaping at the shaft 21. A threaded throat 22 for attachment of a prothesis sleeve is arranged on the upper side of the pump housing 1.

On the detailed figures concerning the pump housing 1, FIG. 3 shows a view from the side, FIG. 4 shows a view from above, FIG. 5 shows a a central section taken along in FIG. 4, FIG. 6 shows a view from the front while FIGS. 7A and 7B show section I—I and section II—II respectively.

With reference to FIGS. 3–5, the main part of the pump housing 1 is seen from above and includes a rectangular part 31, from which the threaded throat 22 and two side parts 32 and 33 extends. The threaded throat 22 contains a bevelled surface 34 reaching from the threaded area to a central, countersinked surface 35. The two side parts 32 and 33 are drilled for the pivot point axis 3 and between them is a space for the back link 11 for three pivot points.

As appears from FIGS. 6, 7A and 7B, two longitudinal channels 40 and 41 are drilled from the front end of the pump housing 1 parallel to the cylindrical drill hole 23. The channels 40 and 41 are at 42, 43, 44 and 45, respectively in connection with transversal channels 46, 47, 48 and 49 which in turn emerge into the central drill hole 23. Preferably one more transversal channel 50 can be arranged and be in communication with the channel 40. See further the description in connection with FIG. 10.

Figure 8:
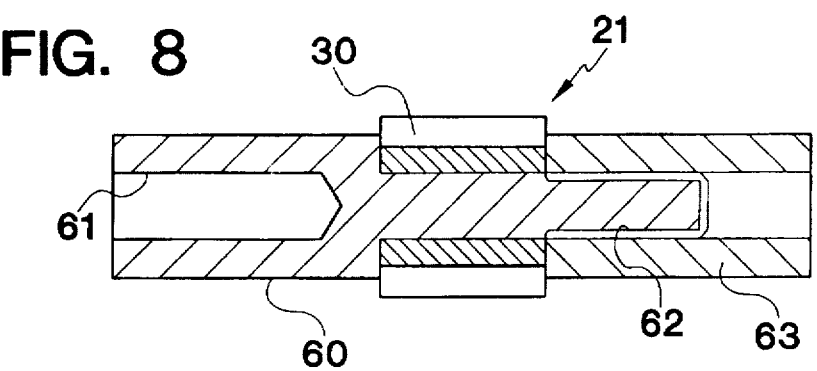
FIG. 8 shows the shaft with the gear-wheel of FIG. 2.

As can be seen in FIG. 8, the shaft 21 is composed of a screw 60 with a main part forming one end of the shaft provided with an internally threaded hole 61, the gear-wheel 30 threaded on to the screw 60 and a longish nut sleeve 63 threaded on the thread of the screw 62 forming the other end of the shaft 21. The screw 60, the gear-wheel 30 and the nut 60 sleeve 63 are joined together making a strong, integrated part, for instance with a thread glue. It is also possible to make the part in such a manner that the gears do not reach out of the perimeter of the shaft, whereby the shaft and the central gear-wheel preferably are made in one piece.

Figure 9A:
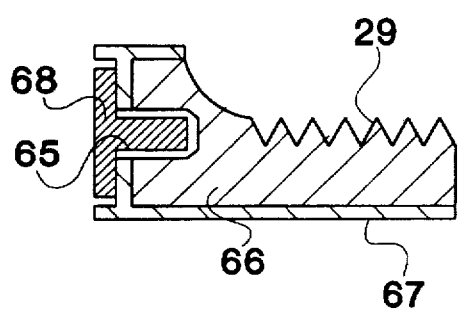
FIG. 9A shows the piston with rack in FIG. 2.

As shown in section in FIG. 9A the piston 20 is preferrably made of one metal piece 66, and one sleeve part 67 surrounding the front and cylindrical part of the metal piece and that partly cylindrical part otherwise forming the rack-gearing 29. The sleeve part 67 is preferrably made of a material with good sealing and wearing qualities, even if a metal chip or the like is present. Examples of such materials are polyacetate and polyurethane plastics. The piston part of the metal piece 66 is provided with a threaded hole 65 into which a screw 68 is threaded holding the sleeve part 67.

Figure 9B:
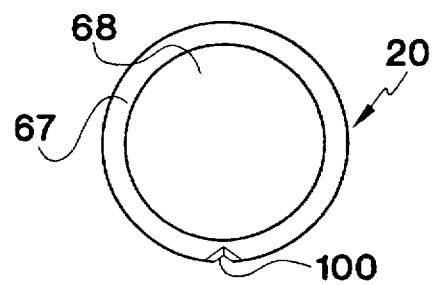
FIG. 9B shows an end view of the piston.
Figure 10:
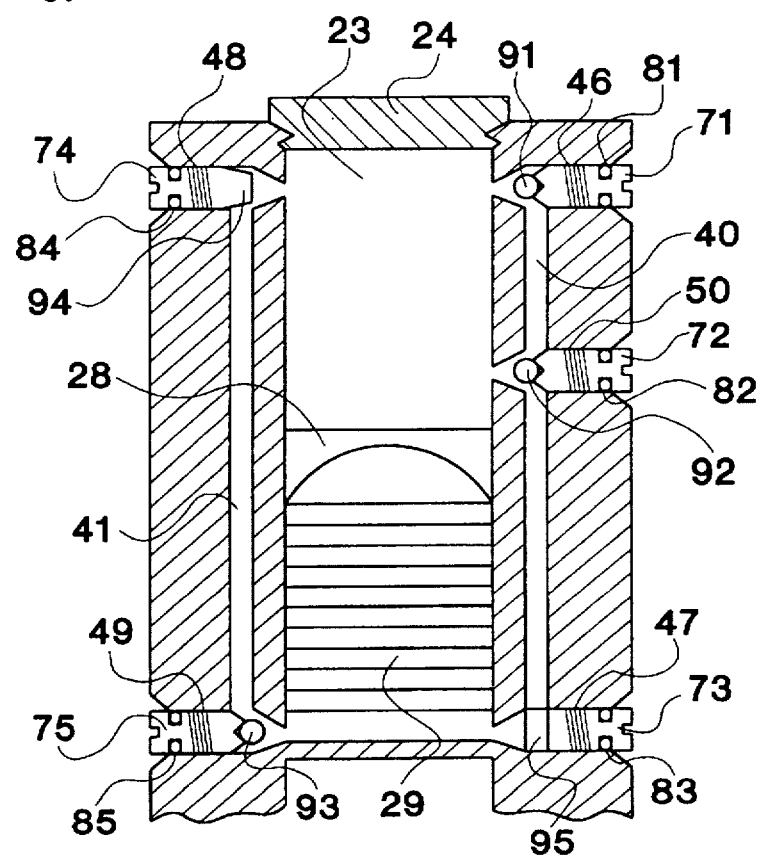
FIG. 10 shows how channels and valves are arranged in the pump house.

The function of the channels 40 and 41 and the transversal channels and their connections with the hydraulic cylinder is shown in detail in FIG. 10. The transversal channels 46–50 are adapted for taking up adjustable screws 71–75 fitted with sealings in the form of o-rings 81–85 placed in grooves. The adjustment screws 71,72 and 75 are designed with ball seats and balls 91,92 and 93 working as chokes and back valves, while the adjustment screws 73 and 74 at the outlets are provided with filter 95 and magnet 94 respectively for ensuring a good function. The damping function of the device is such that when the piston 27 moves upwards in the figure, corresponding to a movement backwards of the shank, the movement is first damped depending on the adjustment of the adjustment screws 71 and 72 and thereafter, when the piston has moved past the outlet at the adjustment screw 72, the movement is damped stronger due to the choke at the adjustment screw 71 alone. In order to get a smooth change-over when the damping is increased the sleeve part 67 of the piston 20 can be shaped with a wedge-formed groove 100 in FIG. 9B tapering from the end of the piston at that part of the piston which is moving past the outlet at the adjustment screw 72. Movement in the other direction is damped only by the choke at the adjustment screw 75. In order to prevent damages if too heavy a choke is adjusted with the adjustment screws 71, 72 or 75, one or more security valves, for example in the form of spring loaded ball valves, may also be arranged in order to put an upper limit to the pressure difference between both sides of the piston 20.

Instead of the adjustment screws 71, 72 and 75, which together with ball seats and the balls 91, 92 and 93 both act as chokes and back valves, conventional back valves with spring loaded balls can be used, whereby no adjustable choke is achieved by the screws 71, 72 and 75 but the degree of damping is constant depending on the dimensions of the channels with possible permanent chokes, or adjustable in another way.

One embodiment of the invention has now been described in detail. The invention can be carried out in many different ways, for example may damping cylinders according to the invention be used with a lot of different types of joints. The scope of the invention is only to be restricted by the wording of the claims.

I claim:

1. A combination of an artificial knee joint and a device for damping turning movement in the artificial knee joint, the artificial knee joint having at least one pivot point, the combination comprising the artificial knee joint having a first link and a second link and the device for damping comprising:

a piston having a rack-gearing along one side thereof;

a hydraulic cylinder having a longitudinal opening in which the piston is mounted, the piston being completely contained within the cylinder, the piston being reciprocable in the hydraulic cylinder, the cylinder further having channels interconnecting opposed ends of the cylinder on opposite sides of the piston whereby hydraulic fluid can flow therethrough upon movement of the piston;

means on an end of the cylinder for mounting the first link of the artificial joint to the hydraulic cylinder;

means for resisting movement of the hydraulic fluid through the channels, the means for resisting including back valves for causing hydraulic fluid to flow in different channels for each direction of movement of the piston; and a shaft having a gear mounted thereon, the shaft extends into the cylinder and the gear meshes with the rack-gearing of the piston, only the shaft extends from an interior of the hydraulic cylinder while the piston and means for resisting are contained within the cylinder, and wherein the second link of the artificial joint is mounted to the shaft, movement of the shaft moving the hydraulic cylinder and thereby forcing hydraulic fluid through the channels of the cylinder, the means for resisting movement resisting flow of hydraulic fluid to dampen movement of the shaft.

2. The combination according to claim 1, wherein the device further comprises at least one adjustable choke in at least one of the channels.

3. The combination according to claim 2, wherein at least one of the channels has an intermediate outlet connected to the longitudinal opening between the ends of the cylinder, the intermediate outlet having an adjustable choke therein for selective damping for different segments of turning movement.

4. The combination according to claim 1, wherein at least one of the channels has an intermediate outlet connected to the longitudinal opening between the ends of the cylinder, the intermediate outlet having an adjustable choke therein for selective damping for different segments of turning movement.

5. The combination according to claim 1, wherein the means for resisting movement includes adjustable chokes and the back valves whereby an amount of flow of hydraulic fluid can be adjusted to thereby adjust a degree of damping and wherein at least one intermediate outlet is provided connecting one of the channels to the longitudinal opening between the ends of the cylinder, the intermediate outlet being closed by the piston when the piston moves in the longitudinal opening.

6. The combination according to claim 5, wherein the piston has a wedge-shaped groove extending from a front end thereof, the wedge-shaped groove being positioned opposite to the intermediate outlet and providing a smooth closing of the intermediate outlet when the piston is moved.

7. The combination according to claim 1, wherein the artificial joint is a polycentric joint with a plurality of pivot points and wherein the hydraulic cylinder has a first pivot point at the means for mounting a first link and a second pivot point where the shaft extends.

8. The combination according to claim 1, wherein the artificial joint is a polycentric joint with seven pivot points and wherein the hydraulic cylinder has a first pivot point at the means for mounting a first link and a second pivot point where the shaft extends.

9. The combination according to claim 1, wherein the artificial joint is a polycentric joint with seven pivot points.

10. The combination according to claim 1, wherein the hydraulic cylinder has means for attaching a prothesis sleeve mounted on an exterior side thereof.

11. The combination according to claim 10, wherein the means for attaching a prothesis sleeve comprises a threaded throat.

12. The combination according to claim 1, wherein the hydraulic cylinder has a detachable lid mounted at one end of the longitudinal opening, the means for mounting a first link being at an opposite end of the cylinder from the detachable lid.

13. The combination according to claim 1, wherein the longitudinal opening of the cylinder extends perpendicularly to the shaft and wherein the channels interconnecting the opposed ends of the cylinder extend parallel to the longitudinal opening.

14. The combination according to claim 1, wherein the piston includes a central metal piece partially surrounded by a sleeve, the rack-gearing being in the metal piece and wherein the piston further includes a screw holding the sleeve and metal piece together.

15. The combination according to claim 1, wherein the shaft comprises a screw having an internally threaded hole, the gear being mounted on an end of the screw and a nut sleeve being provided on the end of the screw to hold the gear on the screw.

* * * * *